United States Patent [19]
Ghosh et al.

[11] Patent Number: 4,696,746
[45] Date of Patent: Sep. 29, 1987

[54] TWO PHASE ANAEROBIC DIGESTION

[75] Inventors: Sambhunath Ghosh, Homewood; David P. Chynoweth, St. Charles; Paul B. Tarman, Elmhurst, all of Ill.

[73] Assignee: Institute of Gas Technology, Chicago, Ill.

[21] Appl. No.: 666,332

[22] Filed: Oct. 30, 1984

[51] Int. Cl.$^4$ ............................................. C02F 11/04
[52] U.S. Cl. .................... 210/603; 210/218; 210/253; 48/197 A; 435/167
[58] Field of Search ....................... 210/603, 218, 253; 48/197 A; 435/167, 801

[56] References Cited

U.S. PATENT DOCUMENTS

| | | | |
|---|---|---|---|
| 3,383,309 | 5/1968 | Chandler | 210/603 |
| 4,022,665 | 5/1977 | Ghosh et al. | 210/603 |
| 4,289,625 | 9/1981 | Tarman et al. | 210/603 |

FOREIGN PATENT DOCUMENTS

| | | | |
|---|---|---|---|
| 3243103 | 5/1984 | Fed. Rep. of Germany | 435/167 |
| 56-51293 | 5/1981 | Japan | 210/603 |
| 58-38239 | 8/1983 | Japan | 210/603 |

*Primary Examiner*—Benoit Castel
*Attorney, Agent, or Firm*—Thomas W. Speckman

[57] ABSTRACT

A two phase anaerobic digestion process for production of methane from organic carbonaceous material in which an active acid forming microbial population is maintained in a first acid forming digestion phase and an active methane forming microbial population is maintained in a second methane forming digestion phase, the liquid effluent from the acid forming digestion phase being passed to a first methane forming digester and gaseous product from the acid forming digestion phase being passed to a second separated methane forming digester for production of methane in the first and second methane forming digesters of the methane forming digestion phase. The two separated methane digestion phases provide increased overall methane production.

20 Claims, 3 Drawing Figures

TWO PHASE ANAEROBIC DIGESTION

BACKGROUND OF THE INVENTION

1. Field of the Invention

This invention relates to improved two phase anaerobic digestion having separated acid and methane forming phases which converts biomass to desired methane product gas with high efficiency and enhances the methane content of product gas by feeding the gas product and the liquid product of the acid forming phase to separated methane phase digesters.

2. Description of the Prior Art

Anaerobic digestion has been known to stabilize sludge and other predominantly organic materials, and usable product gas, of varying composition, has been obtained from such anaerobic digestion processes. The organic feed mixture which provides the substrate for anaerobic biodegradation may comprise a wide variety of organic carbon sources, ranging from raw sewage sludge to municipal refuse, or biomass material such as plants and crop wastes. The process of anaerobic digestion biodegrades any of these organic carbonaceous materials, under appropriate operating conditions, to product gas which contains desirable methane gas.

Separated two phase anaerobic digestion processes have been found to enhance the conversion efficiency, such as described in Pohland and Ghosh, Biotechnol and Bio-Eng. Symp. No. 2, 85-106 (1971), John Wiley & Sons, Inc., and by the same authors in Environmental Letters, 1 (4), 255-266 (1971), Marcel Dekker, Inc. In an acid first phase, the microbial population and operating conditions are selected to promote the conversion of organic carbonaceous matter to volatile fatty acids of low molecular weight. The volatile fatty acids remain solubilized in the liquid portion of the digester contents. The liquid and solid effluent from the acid phase is conveyed to a methanae second phase, where methanogenic microorganisms convert the volatile fatty acids to product gas composed primarily of methane and carbon dioxide. Product gas is removed from the methane phase and processed, or scrubbed, to separate the methane component which is drawn off as pipeline gas. The gas separation of methane is an expensive process which detracts from the economic feasibility of the anaerobic biodegradation of organic carbonaceous material to produce methane gas.

U.S. Pat. No. 4,022,665 discloses certain specific operating conditions for a two phase anaerobic digestion process, such as feed rates and detention times, which promote efficient conversion of organic material. Additionally, the '665 patent discloses two separated methane phases, a methane phase II operated in series with methane phase I. The methane phase II receives effluent fluid and/or effluent gas from the methane phase I. The improved process of the present invention employs two discrete methane producing reactors which operate in parallel. All improvements disclosed in U.S. Pat. No. 4,022,665 can be adapted for use according to the improved process of this invention and the teachings of that patent are incorporated herein by reference.

U.S. Pat. No. 3,383,309 teaches that the rate and efficiency of the anaerobic digestion process, particularly in the methane forming phase, are increased when hydrogen gas is introduced into the digester sludge. According to the '309 patent, hydrogen gas is introduced into both the acid forming and the methane forming phases, to increase the availability of energy-rich "hypersludge". A portion of the product gas removed from the reactor is thermally cracked in a gas reformer and molecular hydrogen and carbon monoxide are returned to the digester.

SUMMARY OF THE INVENTION

The improved process of the present invention uses a two phase anaerobic digestion reaction with two discrete methane phase digesters operated in parallel. Gaseous effluent from the acid phase digester comprising, preferably, high levels of molecular hydrogen, is conveyed to one methane phase digester where the biomethanation of carbon dioxide and hydrogen takes place to yield methane product gas and the liquid product from the acid phase is conveyed to a separate second methane phase digester where biomethanation of predominately fatty acids takes place.

Any organic carbonaceous material which is susceptible to anaerobic biodegradation may be used as feed. The organic carbonaceous feed is continuously or intermittently introduced into a first acid phase digester, where the microbial population comprises various species which convert organic substrate to aldehydes, alcohols and fatty acids such as acetic acid, propionic acid and butyric acid. Since different microbial species facilitate each step of the conversion of organic solids to volatile fatty acids, the microbial population in the acid phase is mixed and conversion to different volatile fatty acids and various intermediates occurs simultaneously. The volatile fatty acid product of the acid phase digestion remains solubilized in the liquid digester contents while produced carbon dioxide, molecular hydrogen and methane are released as gaseous products. Operational conditions are adjusted to favor the bacterial population for desired acid production. Organic carbonaceous feed is continuously or intermittently introduced to the acid phase digester at a rate of about 0.2 to about 10 lbs. of total organics per cubic foot per day and the digester operated with a detention time in the acid phase of about 1 hour to about 5 days, the pH at about 4 to 8, preferably at about 5 to about 7, and under mesophilic or thermophilic anaerobic fermentation conditions.

The improved process of this invention employs two discrete methane producing digesters which operate in parallel. Liquid and solid effluent from the acid phase digester, enriched in volatile fatty acids, is conveyed to a methane phase I digester. The operating conditions and microbial population facilitate the formation of product gas, primarily methane and carbon dioxide, from volatile fatty acids. Again, operating conditions are adjusted to favor the desired bacterial population. Organic carbonaceous feed is introduced continuously or intermittently to achieve a loading rate of about 0.1 to 5 pounds of total organics per cubic foot per day, the detention time in methane phase I is from about 2 to about 15 days, and the pH is maintained at about 6.0 to about 8.0. The gaseous product is removed from methane phase I for methane collection, and the liquid/solid feed effluent is removed for disposal, further processing, or recycling.

Gaseous effluent from the acid phase digester, comprised primarily of carbon dioxide and molecular hydrogen, is conveyed to a methane phase II digester. The operating conditions and the microbial population are selected to favor the biomethanation of carbon dioxide and molecular hydrogen to form methane. Gases are introduced into the methane phase II digester continuously or intermittently, providing a loading of about 0.5 to about 30 volume gas per culture volume per day, detention time in methane phase II is about 2 hours to about 7 days, and the pH of the methane phase II digester is about 6.5 to about 8.5. The gaseous product is removed from methane phase II for methane collection, and the liquid effluent is removed for disposal, further processing or recycling.

According to one embodiment of the present invention, gaseous product from the acid phase digester is conveyed to a separator which provides a hydrogen-rich gas which is subsequently conveyed to the methane phase II digester while the remaining carbon dioxide-rich gas may be recycled into the acid phase digester to promote the conversion of organic solids to volatile fatty acids.

According to another embodiment of the present invention, the gaseous products from methane phase I digester and/or methane phase II digester, or a portion thereof, may be recycled to their respective methane phase digesters for further digestion to yield a product of higher methane content. The methane portion of the gaseous product is insoluble in the digester liquids, and therefore is simply released again as methane gas. The carbon dioxide portion of the gaseous effluent, however, becomes solubilized in the digester and may undergo anaerobic biodegradation to form desirable methane product gas. Additionally, recycling gaseous effluent to the anaerobic digesters provides a mixing means which promotes better liquids/solids mixing.

According to another embodiment, the methane phase II digester may additionally receive a controlled amount liquid/solid effluent from the methane phase I digester, and thus operates in series with the phase I digester, but its primary function is still to biomethanate gaseous effluent from the acid phase digester.

It is an object of the present invention to collect increased amounts of methane in the product gas from the anaerobic digestion of organic carbonaceous material.

It is another object of this invention to obtain higher efficiencies in the anaerobic biodegradation of organic carbonaceous material to methane gas.

It is yet another object of this invention to identify anaerobic digester operating conditions which favor the microbial populations and high efficiency anaerobic biodegradation of separated methane phase digesters fed liquid and gas, separately, from an acid phase digester.

BRIEF DESCRIPTION OF THE DRAWINGS

These and other objects, advantages and features of this invention will be apparent from the description together with the drawings wherein.

DESCRIPTION OF PREFERRED EMBODIMENTS

The process of this invention is applicable to many types of organic feed materials. The term "organic carbonaceous feed material" as used in this disclosure and the appended claims means any type of organic carbonaceous material such as sewage sludge, municipal waste, animal waste, industrial waste, forestry waste, agricultural waste, water and land plants, and other highly organic carbonaceous matter. Mechanical degradation of the feed material may be required to achieve the wide range of particle sizes suitable for use in anaerobic digestion according to this invention. Such mechanical degradation is well known to the art. Various pretreatment of the feed material may advantageously be used with the present invention, such as acid or alkaline hydrolysis.

Figure 1:
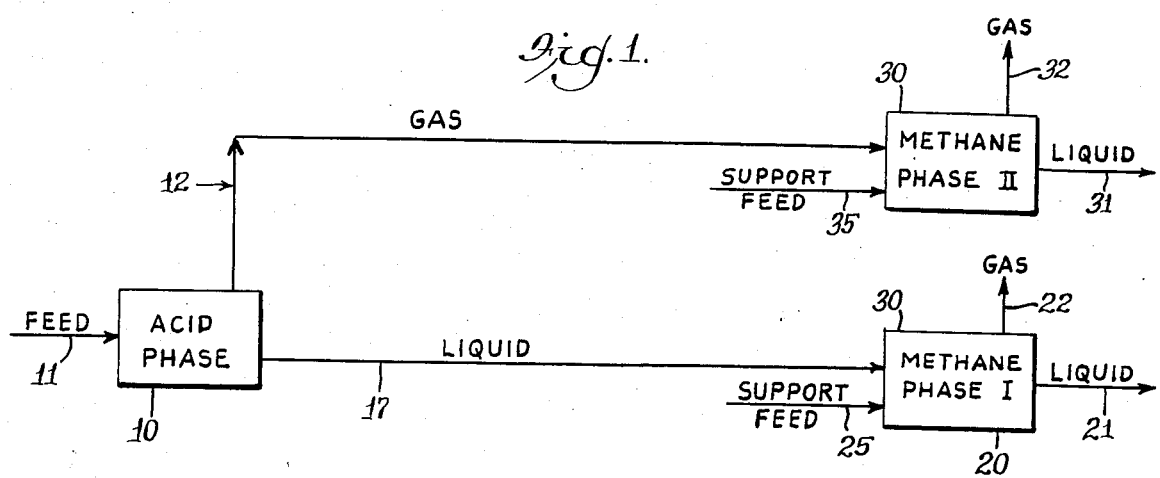
FIG. 1 is a highly schematic block diagram illustrating features of one embodiment of this invention.

As shown in FIG. 1, a source of organic feed material is continuously or intermittently delivered through feed supply line II to acid phase digester 10 at a rate of about 0.2 to about 10 pounds of total organics per cubic foot per day, preferably about 0.8 to about 1.5 pounds. For particulate feeds, higher loading rate ranges may be suitable for soluble highly biodegradable feed materials. The acid phase digester contains a mixed microbial population. Each of the numerous species contained therein facilitates the biodegradation of organic material to volatile fatty acids or an aldehyde or alcohol intermediate. The contents of the acid phase digester are continously or intermittently agitated to promote high digestion. Alternatively, unmixed digesters can be used.

Any active methane producing mesophilic or thermophilic anaerobic digestion system may be used in the process of this invention. Methane-producing anaerobic systems utilizing acid forming bacteria and methane-producing organisms, as are well known to be employed to produce methane from sewage sludge, can be employed in the practice of the present invention. A review of the microbiology of anaerobic digestion is set forth in Anaerobic Digestion, 1. The Microbiology of Anaerobic Digestion, D. F. Toerien and W. H. J. Hattingh, Water Research, Vol. 3, pages 385–416, Pergamon Press (1969). As set forth in that review, the principal suitable acid forming bacteria include species from genera including Aerobacter, Aeromonas, Alcaligenes, Bacillus, Bacteroides, Clostridium, Escherichia, Klebsiella, Leptospira, Micrococcus, Neisseria, Paracolobactrum, Proteus, Pseudomonas, Rhodopseudomonas, Sarcina, Serratia, Streptococcus and Streptomyces. Mixed cultures usually provide the most complete fermentation action. Nutritional balance and pH adjustments may be made as is known to the art to favor hydrolytic action.

The organic carbonaceous feed material in acid phase digester 10 is anaerobically fermented under mesophilic, 15° to 45° C., or thermophilic, 45° to 70° C., temperatures, a pH of about 4 to 8, preferably a pH of about 5 to 7, and for a detention time of about 1 hour to about 5 days, depending on the type of organic carbonaceous feed material introduced. The biodegradable portion of the organic carbonaceous feed material is converted to volatile fatty acids, alcohols and other solubles which remain solubilized in the liquid digester contents, and gaseous products, principally hydrogen and carbon dioxide.

Supernatant from liquid digester contents of acid phase digester 10 is conveyed through liquid conduit 17 to methane phase I digester 20. The liquid may be continuously or intermittently introduced into methane phase I digester 20 at a loading rate of about 0.1 to about 5 pounds of total organics per cubic foot per day, preferably about 0.3 to about 2 pounds of total organics per cubic foot per day. The microbial population maintained in digester 20 is mixed and favors the biodegradation of volatile fatty acids to methane-rich product gases. Support feed containing fresh nutrients and desired chemicals may be delivered to digester 20 through conduit 25. The contents of digester 20 are continuously or intermittently agitated or alternatively, the digester may be unmixed.

Methane phase I digester 20 may utilize methane producing microorganisms which favor production of methane from volatile acids formed in the acid phase digester. The mixed culture of microorganisms in the methane phase I digester may be fed through conduit 25 support feed, nutrients, enzymes, and pH adjusting chemicals to enhance the growth of desired volatile acid utilizing methane forming bacteria. Suitable volatile acid utilizing methane bacteria include Methanobacterium, Methanococcus, Methansarcina and other genuses. The liquid product from acid phase digester 10, rich in volatile acids, is anaerobically fermented in methane phase I digester 20 under mesophilic, 15° to 45° C., or thermophilic, 45° to 70° C., temperatures, a pH between about 6.0 and about 8.0, preferably a pH of between about 6.8 and about 8.0, and for a detention time of about 2 days to about 15 days, preferably for about 3 days to about 6 days, depending upon the volatile acids and microorganism culture. The gaseous product, comprised primarily of methane and carbon dioxide, is removed through gaseous product conduit 22 for delivery to a fuel utilization means or storage or recycle. The liquid and solid effluent is removed from digester 20 through liquid product conduit 21 for further processing, recovery or recycling. Any non-biodegradable components in this effluent can be treated by conventional means.

The gaseous product of acid phase digester 10 is conveyed through gas conduit 12 to methane phase II digester 30. The gas may be continuously or intermittently fed into methane phase II digester 30 at a loading rate of about 0.5 volume of gas per culture volume per day to about 30 volumes gas per culture volume per day, preferably about 1 to about 10 volume of gas per culture volume per day. The microorganism population sustained in methane phase II digester 30 is mixed and favors the biomethanation of carbon dioxide and molecular hydrogen to form methane gas. Alternatively, gas (feed) mixing may be relied upon for mixing. Support feed, enzymes, nutrients, and pH adjusting chemicals to enhance the growth of desired hydrogen and carbon dioxide utilizing bacteria may be fed through conduit 35. The contents of digester 30 are continuously or intermittenly agitated or mixed with the feed gases to achieve high efficiency biomethanation.

Methane phase II digester 30 may utilize methane producing microorganisms which favor production of methane from hydrogen and carbon oxides formed in the acid phase digester. Suitable hydrogen and carbon oxides utilizing methaneforming bacteria include suitable mixed flora of the Methanobacterium, Methanococcus, and other genuses. The anaerobic fermentation conducted in methane phase II digester 30 takes place under mesophilic, 15° to 45° C., or thermophilic, 45° to 70° C., temperatures, a pH of about 6.5 to about 8.5, preferably a pH of about 7.5 to about 8.5, and for a detention time of about 2 hours to about 7 days, preferably about 5 hours to about 1 day, depending upon the feed composition, nutrient condition, fermentation temperatures, and pH, The gaseous product, comprising primarily methane, is removed through gas product conduit 32 for delivery to a fuel utilization means or storage, or recycle. The liquid effluent is removed through liquid product conduit 31 for further processing, recovery, or recycling.

Figure 2:
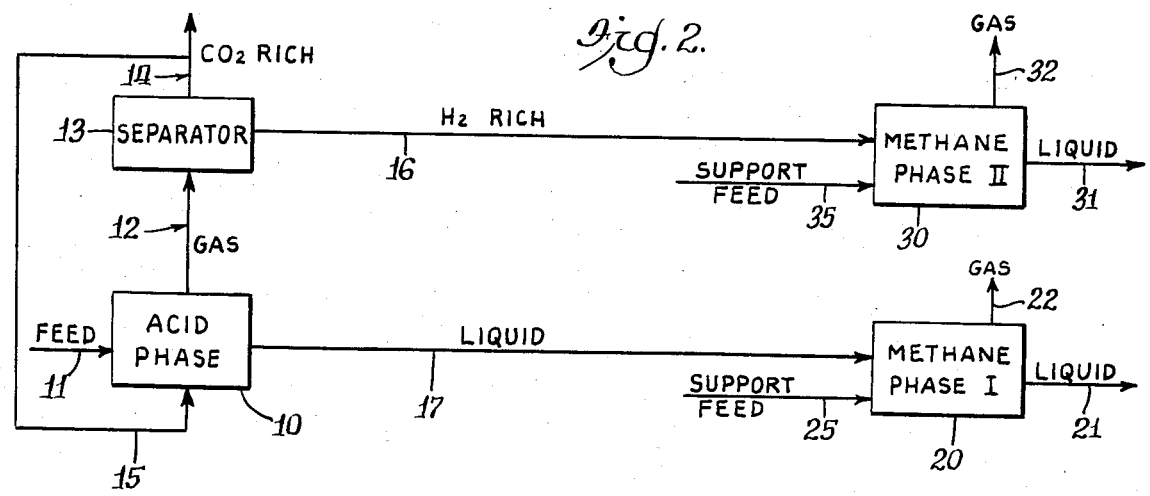
FIG. 2 is a highly schematic block diagram illustrating another embodiment of the invention.

In an alternative embodiment shown in FIG. 2, gas product from acid phase digester 10 is conveyed by conduit 12 to separator 13. Separator 13 may be any separator known to the art which can separate gas comprised primarily of carbon dioxide and molecular hydrogen into a hydrogen-rich and a carbon dioxide-rich stream. The gas stream enriched in molecular hydrogen is conveyed through conduit 16 to methane phase II digester 30. The methane producing bioconversion process which takes place in methane phase II digester 30 is generally limited by the shortage of molecular hydrogen. Thus, by providing hydrogen-rich gas to methane phase II digester 30 the conversion efficiency of the biomethanation process is significantly increased. Hydrogen gas may be obtained from the process residue by several suitable thermal processes and added to hydrogen-rich gas fed to methane phase II digester 30. Moreover, the separation of carbon dioxide and molecular hydrogen is generally more efficiently achieved than the separation of carbon dioxide from methane. This embodiment, by increasing the conversion efficiency of carbon dioxide to methane in methane phase II digester 30, reduces the amount of carbon dioxide present in the product gas, thereby reducing or eliminating the necessity for costly separation processes to enhance the methane content of the product gas. The carbon dioxide component may be removed from separator 13 and delivered through conduit 14 for other uses. Alternatively, the carbon dioxide component may be conveyed through recycle conduit 15 and reintroduced to acid phase digester 10 for enhancement of acid phase digestion.

Figure 3:
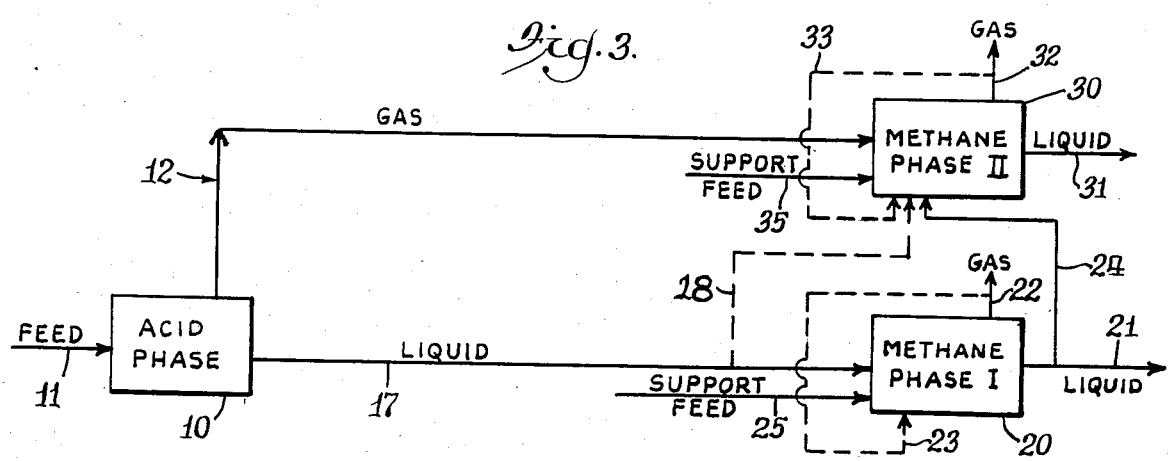
FIG. 3 is a highly schematic block diagram illustrating another embodiment of the invention, the dotted lines representing alternative embodiments.

In another alternative embodiment shown in FIG. 3, at least a portion of the liquid effluent removed from methane phase I digester 20 is conveyed through conduit 24 and introduced into methane phase II digester 30 to provide additional substrate material for the methane phase II digestion. Solubilized carbon dioxide comprises a substantial portion of the methane phase I liquid effluent. In the phase II digestion, this additional carbon dioxide combines with molecular hydrogen to form additional methane product. The methane phase I liquid effluent contains the necessary macronutrients (N, P, S), alkaline earth metals (N, K, Ca, Mg, etc.), metals (Ni, Co, Fe, Cd, etc.) for enzyme snythesis, enzymes, and buffering chemicals.

In yet another embodiment of the process of this invention shown in FIG. 3, a portion of the gaseous product from one or both of the methane phase digesters may be recycled and reintroduced into its respective methane phase digester. This recycle feature promotes more efficient conversion to desirable methane product gas and it provides a mixing means for digesters. Any methane gas which is recycled is insoluble in the liquid substrate matrix, and thus remains unaltered as it flows through the matrix and is removed as product gas once again. Other gaseous products, principally carbon dioxide, however, are more soluble and, by recycling, are provided another opportunity to undergo biomethanation to form desirable methane gas. This embodiment thus increases both the conversion efficiency and the methane content of the product gas. This embodiment aids in reducing the required costly cleanup of the product gas and permits use of the product gas in its unrefined form, which provides a higher heating value. The product gas recycle as described above may be used in conjunction with one or both methane phase I and methane phase II digesters with or without passage of liquid product from methane phase I digester to methane phase II digester and with or without gas recycle to the acid phase digester. Any of these embodiments may be used individually or in any combination.

In another embodiment of the process of this invention shown in FIG. 3, a controlled portion of the acid phase liquid effluent may be introduced directly into methane phase II digester 30 through conduit 18 to supply nutrients and organic growth factors produced by the acid forming microorganisms and used by the methane forming organisms. To achieve the desired amount of such materials in methane phase II digester 30, it is suitable that up to about 16 percent of the liquid flow from conduit 17 be diverted through conduit 18 to digester 30. Introduction of a controlled portion of the acid phase liquid effluent to the methane phase II digester as described above may also be used with the embodiments shown in FIGS. 1 and 2.

The process of this invention reduces the sulfide toxicity problems recognized to exist when a plurality of methane digesters are used as in the 4,022,665 patent. The arrangement of the methane digesters in parallel with formed gas from acid forming digester 10 passing to methane phase II digester 30 and liquid effluent from acid forming digester 10 passing to methane phase I digester 20 substantially reduces such sulfide toxicity problems.

It is an important aspect of this invention that in a two phase anaerobic digestion process for production of methane from organic carbonaceous material an active acid forming microbial population is maintained in a first acid forming digestion phase and an active methane forming microbial population is maintained in a second methane forming digestion phase and that liquid effluent from said acid forming digestion phase is passed to a first methane forming digester and gaseous product of said acid forming digestion phase is passed to a second methane forming digester for production of methane in said first and second methane forming digesters comprising said methane forming digestion phase. These two methane digestion phases provide increased overall methane production from a unit amount of carbonaceous material.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A process for improved methane production by two phase anaerobic digestion of organic carbonaceous material comprising the steps:
   introducing said organic carbonaceous material into an acid phase digester at a rate of about 0.2 to about 10 pounds total organics per cubic foot per day;
   maintaining an active acid forming microbial population in said acid phase digester and fermenting said organic carbonaceous material under mesophilic or thermophilic anaerobic conditions and a pH about 4 to about 8 for a detention time of about 1 hour to about 5 days;
   passing liquid/solids effluent from said acid phase digester to a methane phase I digester and passing gaseous product of said acid phase digester only to a separate methane phase II digester operated in parallel with said methane phase I digester; and
   maintaining an active methane forming microbial population in each of said methane phase I and said methane phase II digesters and withdrawing gas comprising methane from each said methane phase I and methane phase II digesters.

2. The process of claim 1 wherein said methane phase I digester is fed said liquid/solids effluent from said acid phase digester at a rate of about 0.1 to about 5 pounds total organics per cubic foot per day, maintained at a pH of about 6.0 to about 8.0, and the detention time is about 2 to about 15 days.

3. The process of claim 1 wherein said methane phase I digester is fed said liquid/solids effluent from said acid phase digester at a rate of about 0.3 to about 2 pounds total organics per cubic foot per day, maintained at a pH of about 6.8 to about 8.0, and the detention time is about 3 to about 8 days.

4. The process of claim 3 wherein said methane phase II digester is fed said gaseous product from said acid phase digester at a rate of about 1 to about 10 volume gas per culture volume per day, maintained at a pH of about 7.5 to about 8.5, and the detention time is about 5 hours to 1 day.

5. The process of claim 1 wherein said methane phase II digester is fed said gaseous product from said acid phase digester at a rate of about 0.5 to 30 volume gas per culture volume per day, maintained at a pH of about 6.5 to about 8.5, and the detention time is about 2 hours to about 5 days.

6. The process of claim 1 wherein said methane phase II digester is fed said gaseous product from said acid phase digester at a rate of about 1 to about 10 volume gas per culture volume per day, maintained at a pH of about 7.5 to about 8.5, and the detention time is about 5 hours to 1 day.

7. The process of claim 1 wherein said gaseous product of said acid phase digester is conveyed to a separator means wherein molecular hydrogen and carbon dioxide are separated and hydrogen-rich gas is conveyed from said separator means to said methane phase II digester.

8. The process of claim 7 wherein carbon dioxide-rich gas from said separator means is recirculated to said acid phase reactor.

9. The process of claim 1 wherein at least a portion of the liquid/solids effluent from said methane phase I digester is conveyed to said methane phase II digester.

10. The process of claim 1 wherein a portion of said liquid/solids effluent from said acid phase digester is conveyed to said methane phase II digester.

11. In a two phase anaerobic digestion process for production of methane from organic carbonaceous material wherein an active acid forming microbial population is maintained in a first acid forming digestion phase and an active methane forming microbial population is maintained in a second methane forming digestion phase, the improvement comprising; passing liquid/solids effluent from said acid forming digestion phase to a first methane forming digester and passing gaseous product of said acid forming digestion phase only to a second methane forming digester operated in parallel with said first methane forming digester for production of methane in said first and second methane forming digesters comprising said methane forming digestion phase.

12. The process of claim 11 wherein said methane phase I digester is fed said liquid/solids effluent from said acid phase digester at a rate of about 0.1 to about 5 pounds total organics per cubic foot per day, maintained at a pH of about 6.0 to about 8.0, and the detention time is about 2 to about 15 days.

13. The process of claim 11 wherein said methane phase I digester is fed said liquid/solids effluent from said acid phase digester at a rate of about 0.3 to about 2 pounds total organics per cubic foot per day, maintained at a pH of about 6.8 to about 8.0, and the detention time is about 3 to about 8 days.

14. The process of claim 13 wherein said methane phase II digester is fed said gaseous product from said acid phase digester at a rate of about 1 to about 10 volume gas per culture volume per day, maintained at a pH of about 7.5 to about 8.5, and the detention time is about 5 hours to 1 day.

15. The process of claim 11 wherein said methane phase II digester is fed said gaseous product from said acid phase digester at a rate of about 0.5 to 30 volume gas per culture volume per day, maintained at a pH of about 6.5 to about 8.5, and the detention time is about 2 hours to about 5 days.

16. The process of claim 11 wherein said methane phase II digester is fed said gaseous product from said acid phase digester at a rate of about 1 to about 10 volume gas per culture volume per day, maintained at a pH of about 7.5 to about 8.5, and the detention time is about 5 hours to 1 day.

17. The process of claim 11 wherein said gaseous product of said acid phase digester is conveyed to a separator means wherein molecular hydrogen and carbon dioxide are separated and hydrogen-rich gas is conveyed from said separator means to said methane phase II digester.

18. The process of claim 17 wherein carbon dioxide-rich gas from said separator means is recirculated to said acid phase reactor.

19. The process of claim 11 wherein at least a portion of the liquid/solids effluent from said methane phase I digester is conveyed to said methane phase II digester.

20. The process of claim 11 wherein a portion of said liquid/solids effluent from said acid phase digester is conveyed to said methane phase II digester.

* * * * *